(12) United States Patent
Choi

(10) Patent No.: US 6,607,868 B2
(45) Date of Patent: Aug. 19, 2003

(54) PHOTORESIST MONOMERS, POLYMERS THEREOF, AND PHOTORESIST COMPOSITIONS CONTAINING THE SAME

(75) Inventor: Jae Hak Choi, Ichon-shi (KR)

(73) Assignee: Hynix Semiconductor Inc., Kyungki-do (KR)

( * ) Notice: Subject to any disclaimer, the term of this patent is extended or adjusted under 35 U.S.C. 154(b) by 156 days.

(21) Appl. No.: 09/888,836

(22) Filed: Jun. 25, 2001

(65) Prior Publication Data

US 2002/0012879 A1 Jan. 31, 2002

(30) Foreign Application Priority Data

Jun. 30, 2002 (KR) .......................... 2000-37227

(51) Int. Cl.[7] .......................... G03F 7/00; C07D 211/30
(52) U.S. Cl. .............. 430/270.1; 430/283.1; 430/313; 430/324; 430/905; 548/538; 546/226
(58) Field of Search .................. 430/270.1, 905, 430/313, 324, 906; 548/538, 530; 546/225, 226

(56) References Cited

U.S. PATENT DOCUMENTS 5,538,666 A * 7/1996 Jin .................... 252/299.01
5,616,669 A * 4/1997 Jin et al. .................. 526/285
6,514,666 B1 * 2/2003 Choi et al. ............... 430/270.1

\* cited by examiner

*Primary Examiner*—Janet Baxter
*Assistant Examiner*—Yvette C Thornton
(74) *Attorney, Agent, or Firm*—Marshall, Gerstein & Borun

(57) ABSTRACT

Dipropargyl acetamide derivatives of following Formula 1 which are photoresist monomers, polymers thereof, and photoresist compositions containing the same. The photoresist polymer has high etching resistance, adhesiveness and post-exposure delay stability. As a result, the photoresist composition is suitable to form a fine pattern in a deep ultraviolet region.

Formula 1

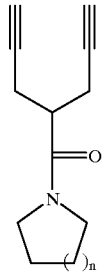

wherein, n is an integer from 0 to 5.

24 Claims, 6 Drawing Sheets

PHOTORESIST MONOMERS, POLYMERS THEREOF, AND PHOTORESIST COMPOSITIONS CONTAINING THE SAME

BACKGROUND OF THE INVENTION

1. Technical Field

Novel photoresist monomers, polymers thereof, and photoresist compositions comprising the polymers are disclosed. More specifically, novel dipropargyl acetamide photoresist monomers, polymers and compositions having excellent post-exposure delay (PED) stability in a deep ultraviolet region are disclosed.

2. Description of the Background Art

In general, a useful photoresist (hereinafter, abbreviated as "PR") has a variety of desired characteristics, such as high light transmissibility at the wavelength of 193 nm, excellent etching resistance, heat resistance and adhesiveness. In addition, a photoresist should be easily developable in a commercially readily available developing solution, such as 2.38 wt % aqueous tetramethylammonium hydroxide (TMAH) solution. However, it is very difficult to synthesize a photoresist polymer that satisfies all of these criteria.

To solve some of the problems described above, much research has been done on a resin having the high transparency at the wavelength of 193 nm and dry etching resistance similar to a novolac resin used in an i-line. For example, IBM has developed the following methacrylate copolymer resin:

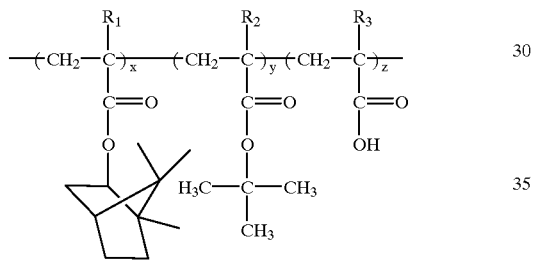

wherein, $R_1$, $R_2$ and $R_3$ are independently H or $CH_3$.

In the above resin, the ratio of "x" must be increased in order to improve the dry etching resistance. However, if the amount of "x" is increased, hydrophilicity of the resin itself is reduced, therefore a thin pattern may collapse. In order to overcome such a disadvantage, hydrophilic monomers such as a methacrylic acid are copolymerized. However, in this case, a photoresist top loss may occur during developing, and thus a special developing solution such as a diluted solution or a solution containing isopropylalcohol must be employed, instead of the currently used developing solution. In addition, if the resin does not contain a predetermined degree of the alicyclic compounds, it cannot satisfy the etching resistance criteria. In addition, the polymer is very sensitive to environment, and thus hard to obtain sufficient post exposure delay (PED) stability.

In general, when there is delay between exposure of the photoresist to light and development of the exposed photoresist, acids that are generated on the exposed area are neutralized by amine compounds which may be present in the production atmosphere. Since the pattern formation depends on acids that are generated by the exposure, neutralization of acids by atmospheric amine compounds reduce, prevent or alter a pattern formation, e.g., a T-topping phenomenon may occur where the top portion of the pattern forms an undesirable T-shape.

SUMMARY OF THE DISCLOSURE

A photoresist monomers having an enhanced PED stability are disclosed.

PR polymers using the PR monomers described above and a process for preparing the same are also disclosed.

Photoresist compositions using the PR polymers described above are also disclosed.

A semiconductor device produced by using the above described PR composition is also disclosed.

DETAILED DESCRIPTION OF THE PRESENTLY PREFERRED EMBODIMENTS

Figure 1:
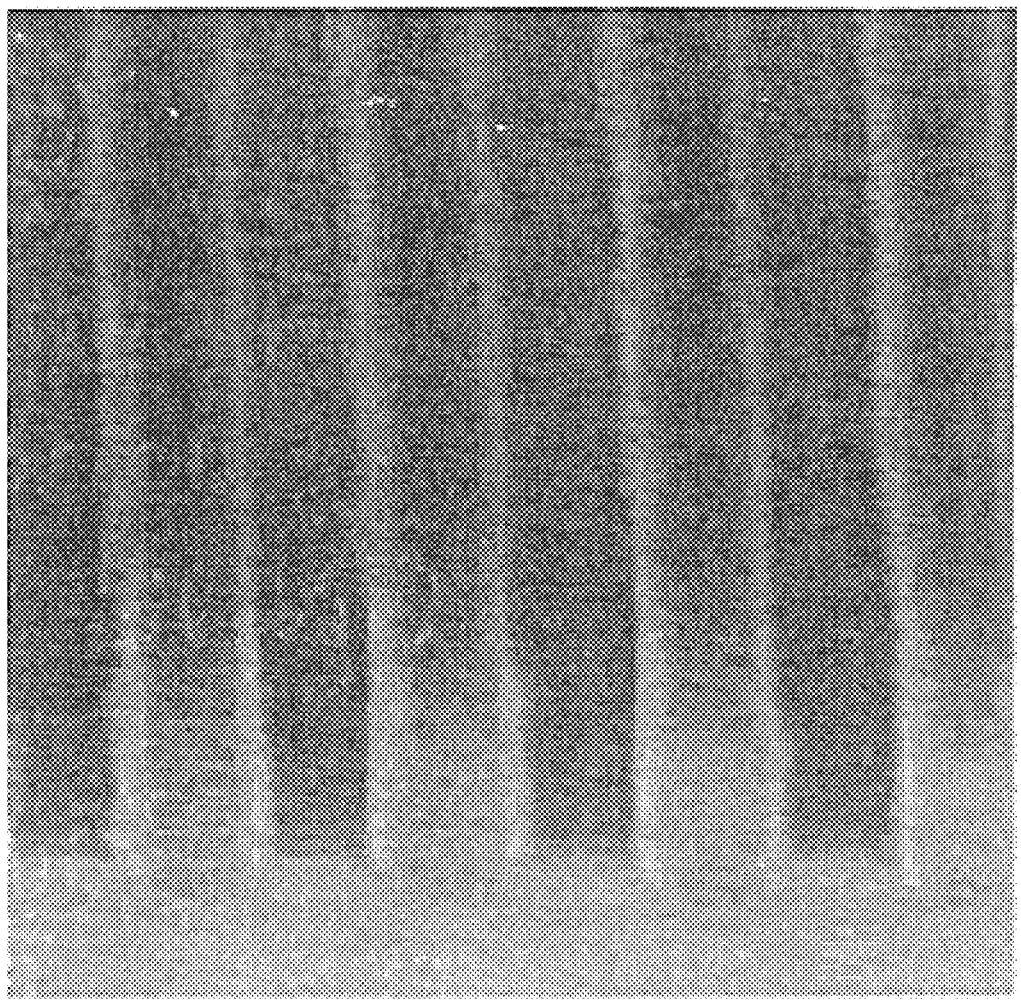
FIGS. 1 to 6 are photographs respectively showing patterns obtained in Examples 9 to 14.

One disclosed photoresist monomer is dipropargyl acetamide derivative of following Formula 1:

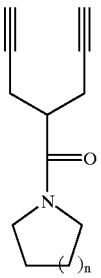

Formula 1 wherein, n is an integer from 0 to 5.

Exemplary compounds of Formula 1 include piperidinyl dipropargyl acetamide of following Formula 1a and pyrrolidinyl dipropargyl acetamide of following Formula 1b.

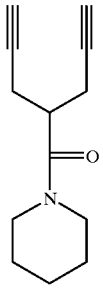

Formula 1a

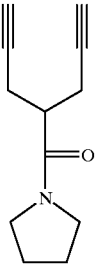

Formula 1b

One disclosed photoresist polymer comprises dipropargyl acetamide of Formula 1 as a first monomer.

The photoresist polymer can further comprise at least one monomer selected from the group consisting of dipropargyl acetic acid ester derivative of following Formula 2 and dipropargyl carbinol of following Formula 3:

Formula 2

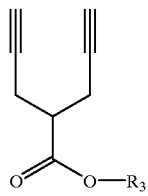

wherein, R₃ is H or an acid labile protecting group.

Formula 3

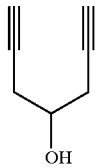

The acid labile protecting group can be any of the known protective groups that can be substituted by an acid and functions to prevent the compound to which the group is bound from dissolving in the alkaline developer solution. Conventional acid labile protecting groups are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Exemplary acid labile protecting groups include substituted or unsubstituted linear or branched ($C_1$-$C_5$) alkyl or alkoxy alkyl. More preferably, the acid labile protecting group is selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl, tert-butoxycarbonyl and 2-acetylmenth-1-yl.

Preferred photoresist polymers include polymers of the following Formulas listed below:

Poly(tert-butyl dipropargyl acetate/dipropargyl carbinol/piperidinyl dipropargyl acetamide) of following Formula 4:

Formula 4

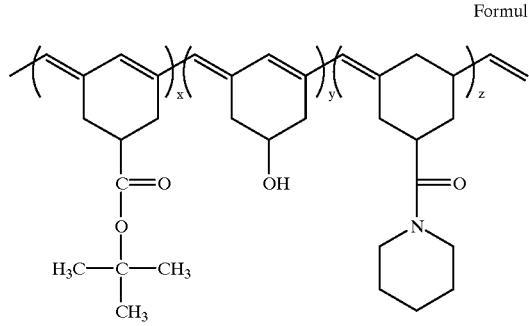

Poly(ethoxyethyl dipropargyl acetate/dipropargyl carbinol/piperidinyl dipropargyl acetamide) of following Formula 5:

Formula 5

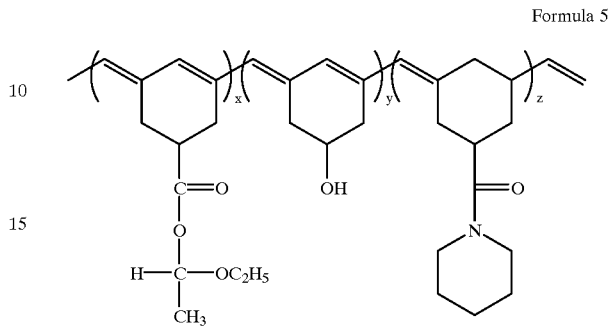

Poly(ethoxypropyl dipropargyl acetate/dipropargyl carbinol/piperidinyl dipropargyl acetamide) of following Formula 6:

Formula 6

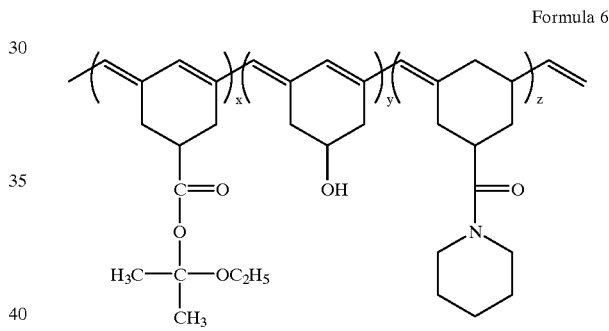

Poly(tert-butyl dipropargyl acetate/dipropargyl carbinol/pyrrolidinyl dipropargyl acetamide) of following Formula 7:

Formula 7

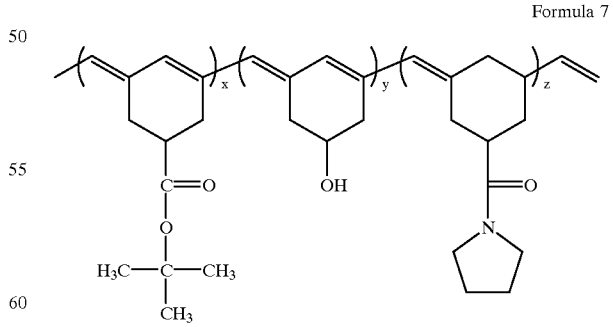

Poly(ethoxyethyl dipropargyl acetate/dipropargyl carbinol/pyrrolidinyl dipropargyl acetamide) of following Formula 8:

Formula 8

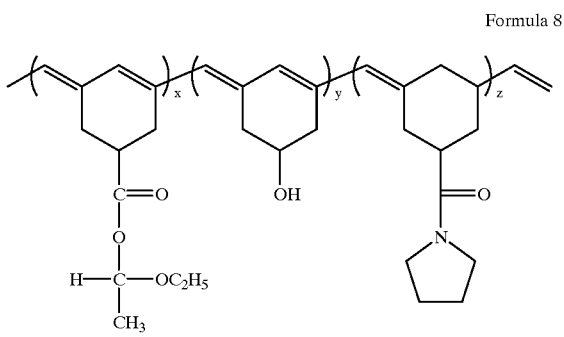

Poly(ethoxypropyl dipropargyl acetate/dipropargyl carbinol/pyrrolidinyl dipropargyl acetamide) of following Formula 9:

Formula 9

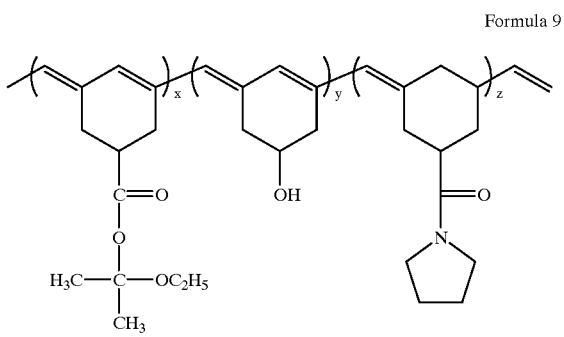

In Formulae 4 to 9, x:y:z fall within or about the ranges 0.01–99mol %: 0.01–99mol %: 0.01–50mol %.

The polymers can be prepared by any of the methods known to one of ordinary skill in the art, including by a metathesis polymerization of monomers with a metathesis catalyst. An exemplary process for preparing a polymer includes the steps of admixing a metathesis catalyst and a photoresist monomer under conditions sufficient to produce the polymer. Preferably, the process further includes dissolving the metathesis catalyst in an organic solvent to produce a catalyst solution. The catalyst solution is then added to a polymerization solvent. After maintenance at a temperature ranging from about 20 to about 40° C. for a time period ranging from about 10 to about 20 minutes, a photoresist monomer is then added to the resulting polymerization solvent. The resulting reaction mixture is then typically heated to produce the polymer.

As stated above, the monomer can be dipropargyl acetamide derivative of Formula 1, or a mixture of dipropargyl acetamide derivative and one or more compound of dipropargyl acetic acid ester derivative of Formula 1a and dipropargyl carbinol of Formula 1b.

The process can also include adding a cocatalyst (preferably as a cocatalyst solution) to the polymerization solvent.

A transition metal-halide or an organometallic compound, some of which are disclosed in EP 0 789 278 (Aug. 13, 1997), can be used as the metathesis catalyst or the cocatalyst. Preferably, a catalyst is selected from the group consisting of $MoCl_5$, $WCl_6$, $Mo(OEt)_5$ and $PdCl_2$. Preferably, a cocatalyst is selected from the group consisting of $(n-Bu)_4Sn$ and $EtAlCl_2$.

The polymerization solvent is preferably selected from the group consisting of chlorobenzene, 1,4-dioxane, dimethylformamide, cyclohexane, tetrachloromethane, tetrahydrofuran and mixture thereof. An organic solvent for producing a catalyst solution or a cocatalyst solution is preferably selected from the group consisting of hexane, tetrahydrofuran, cyclohexane and mixture thereof.

A photoresist composition can comprise a photoresist polymer (i.e., photoresist resin) described above, an organic solvent and a photoacid generator.

Any of known photoacid generator, which is able to generate acids by light, can be used in PR composition of the present invention. Conventional photoacid generators are disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0789 278 (Aug. 13, 1997) and U.S. Pat. No. 6,132,926 (Oct. 17, 2000). Preferably, the photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate dibutylnaphthylsulfonium triflate and mixture thereof. The amount of photoacid generator is from about 0.01 to about 10% by weight of the photoresist polymer employed. It has been found that when the photoacid generator is used in the amount less than about 0.01%, it lowers photosensitivity of the photoresist composition, and when the photoacid generator is used in the amount greater than about 10%, it results in a poor pattern formation due to its high absorption.

While a variety of organic solvents, as disclosed in U.S. Pat. No. 5,212,043 (May 18, 1993), WO 97/33198 (Sep. 12, 1997), WO 96/37526 (Nov. 28, 1996), EP 0 794 458 (Sep. 10, 1997), EP 0 789 278 (Aug. 13, 1997) and U.S. Pat. No. 6,132,926 (Oct. 17, 2000), are suitable for use in the photoresist composition of the present invention, an organic solvent selected from the group consisting of propyleneglycol methyl ether acetate, ethyl lactate, methyl 3-methoxypropionate, ethyl 3-ethoxypropionate, cyclohexanone and mixture thereof is preferred.

The amount of solvent used is preferably in the range of from about 100% to about 1000% by weight of the photoresist polymer. This ratio has been found to be particularly useful in obtaining a photoresist layer of desirable thickness. In particular, it has been found by the present inventors that when the amount of organic solvent is about 500 wt %, a photoresist layer having 0.5 μm of thickness can be obtained.

A method for forming a photoresist pattern comprises the steps of:

(a) coating the above described photoresist composition on a substrate of semiconductor element to form a photoresist film;

(b) exposing the photoresist film to light using a light source; and (c) developing the photoresist film, for example, using an alkaline solution such as 2.38 wt % TMAH solution.

Optionally, the photoresist film can be heated (i.e., baked), preferably to temperature in the range of from about 70° C. to about 200° C., before and/or after the step (b).

Exemplary light sources which are useful for forming the PR pattern include VUV (157 nm), ArF (193 nm), KrF (248 nm), EUV (13 nm), E-beam, X-ray and ion beam. Preferably, the irradiation energy is in the range of from about 1 $mJ/cm^2$ to about 100 $mJ/cm^2$.

In addition, provides a semiconductor device can be manufactured using the photoresist compositions described above.

Additional objects, advantages, and novel features of this disclosure will become apparent to those skilled in the art upon examination of the following examples thereof, which are not intended to be limiting.

I. Preparation of Photoresist Monomer

EXAMPLE 1

Synthesis of Piperidinyl Dipropargyl Acetamide 24.9 g of acetylpiperedine was slowly added into a solution obtained by dissolving 7.8 g of sodium in 150 ml of ethanol at 0° C. The resulting solution was stirred for one hour, and 48 g of propargyl bromide was slowly added thereto. Thereafter, the resulting solution was refluxed for one hour, and ethanol was removed under reduced pressure. The residual solution was diluted using distilled water, and an organic layer was separated. The resulting solution was re-crystallized in hexane, to obtain 32 g of title compound of Formula 1a (yield: 80%).

EXAMPLE 2

Synthesis of Pyrrolidinyl Dipropargyl Acetamide 22.0 g of acetyl pyrrolidine was slowly added into a solution obtained by dissolving 7.8 g of sodium in 150 ml of ethanol at 0° C. The resulting solution was stirred for one hour, and 48 g of propargyl bromide was slowly added thereto. Thereafter, the resulting solution was refluxed for one hour, and ethanol was removed under reduced pressure. The residual solution was diluted using distilled water, and an organic layer was separated. The resulting solution was re-crystallized in hexane, to obtain 26.7 g of title compound of Formula 1b (yield: 75%).

II. Preparation of Photoresist Polymer

EXAMPLE 3

Synthesis of Poly(Tert-butyl Dipropargyl Acetate/ Dipropargyl Carbinol/Piperidinyl Dipropargyl Acetamide)

To a 100-ml-flask was added 10 ml of 1,4-dioxane and 5 mM of $MoCl_5$ solution. After 15 minutes at 30° C. under nitrogen atmosphere, 24.03 g of tert-butyl dipropargyl acetate, 13.52 g of dipropargyl carbinol and 1.3 g of piperidinyl dipropargyl acetamide were slowly added and polymerized at 60° C. for 24 hours. The polymerization reaction was stopped by adding a small amount of methanol. The resultant polymer was dissolved in chloroform and precipitated in methanol. The precipitate was filtered and dried under reduced pressure, to obtain 31.1 g of title polymer of Formula 4 (yield: 80%).

EXAMPLE 4

Synthesis of Poly(Ethoxyethyl Dipropargyl Acetate/ Dipropargyl Carbinol/Piperidinyl Dipropargyl Acetamide)

The procedure of Example 3 was repeated except that 26.03 g of ethoxyethyl dipropargyl acetate was used instead of 24.03 g of tert-butyl dipropargyl acetate, to obtain 31 g of the title polymer of Formula 5 (yield: 75%).

EXAMPLE 5

Synthesis of Poly(Ethoxypropyl Dipropargyl Acetate/Dipropargyl Carbinol/Piperidinyl Dipropargyl Acetamide)

The procedure of Example 3 was repeated except that 27.78 g of ethoxypropyl dipropargyl acetate was used instead of 24.03 g of tert-butyl dipropargyl acetate, to obtain 35 g of the title polymer of Formula 6 (yield: 82%).

EXAMPLE 6

Synthesis of Poly(Tert-butyl Dipropargyl Acetate/ Dipropargyl Carbinol/Pyrrolidinyl Dipropargyl Acetamide)

The procedure of Example 3 was repeated but using 1.2 g of pyrrolidinyl dipropargyl acetamide, instead of piperidinyl dipropargyl acetamide, to obtain 30.0 g of the title polymer of Formula 7(yield: 78%).

EXAMPLE 7

Synthesis of Poly(Ethoxyethyl Dipropargyl Acetate/ Dipropargyl Carbinol/Pyrrolidinyl Dipropargyl Acetamide)

The procedure of Example 4 was repeated but using 1.2 g of pyrrolidinyl dipropargyl acetamide, instead of piperidinyl dipropargyl acetamide, to obtain 29.8 g of the title polymer of Formula 8 (yield: 73%).

EXAMPLE 8

Synthesis of Poly(Ethoxypropyl Dipropargyl Acetate/Dipropargyl Carbinol/Pyrrolidinyl Dipropargyl Acetamide)

The procedure of Example 5 was repeated but using 1.2 g of pyrrolidinyl dipropargyl acetamide, instead of piperidinyl dipropargyl acetamide, to obtain 35 g of the title polymer of Formula 9 (yield: 82%).

III. Preparation of Photoresist Composition and Formation of Pattern

EXAMPLE 9

10 g of polymer prepared in Example 3 and 0.2 g of triphenylsulfonium triflate were dissolved in 50 g of propyleneglycol methyl ether acetate. The resulting solution was filtered through 0.1 μm filter to obtain a photoresist composition.

The photoresist composition was spin-coated on a silicon wafer. The coated wafer was soft-baked at 100° C. for 90 seconds, exposed to light using an ArF laser exposer, post-baked at 120° C. for 90 seconds, and developed in the 2.38 wt % aqueous TMAH solution, to obtain an ultrafine pattern of 0.20 μm L/S (see FIG. 1).

EXAMPLE 10

Figure 2:
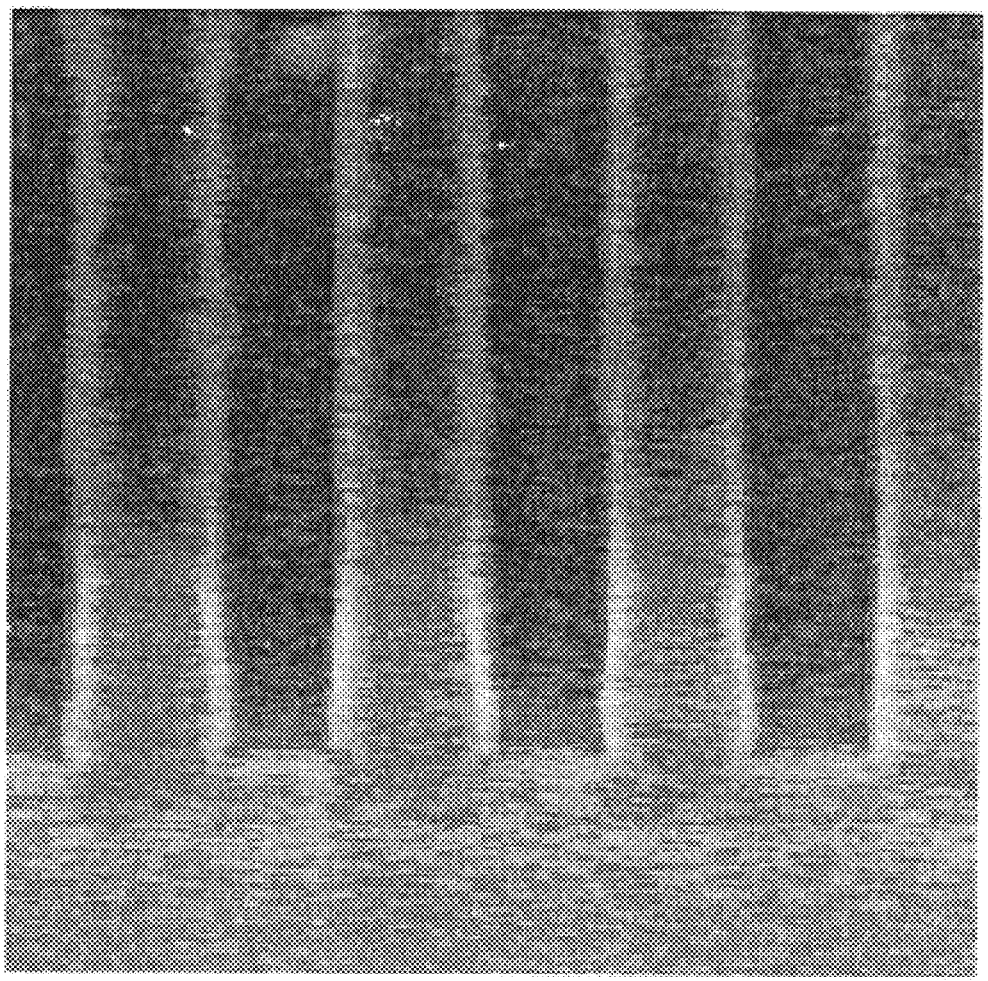

The procedure of Example 9 was repeated but using the polymer of Example 4, instead of the polymer of Example 3 to obtain the pattern of 0.20 μm L/S (see FIG. 2).

EXAMPLE 11

Figure 3:
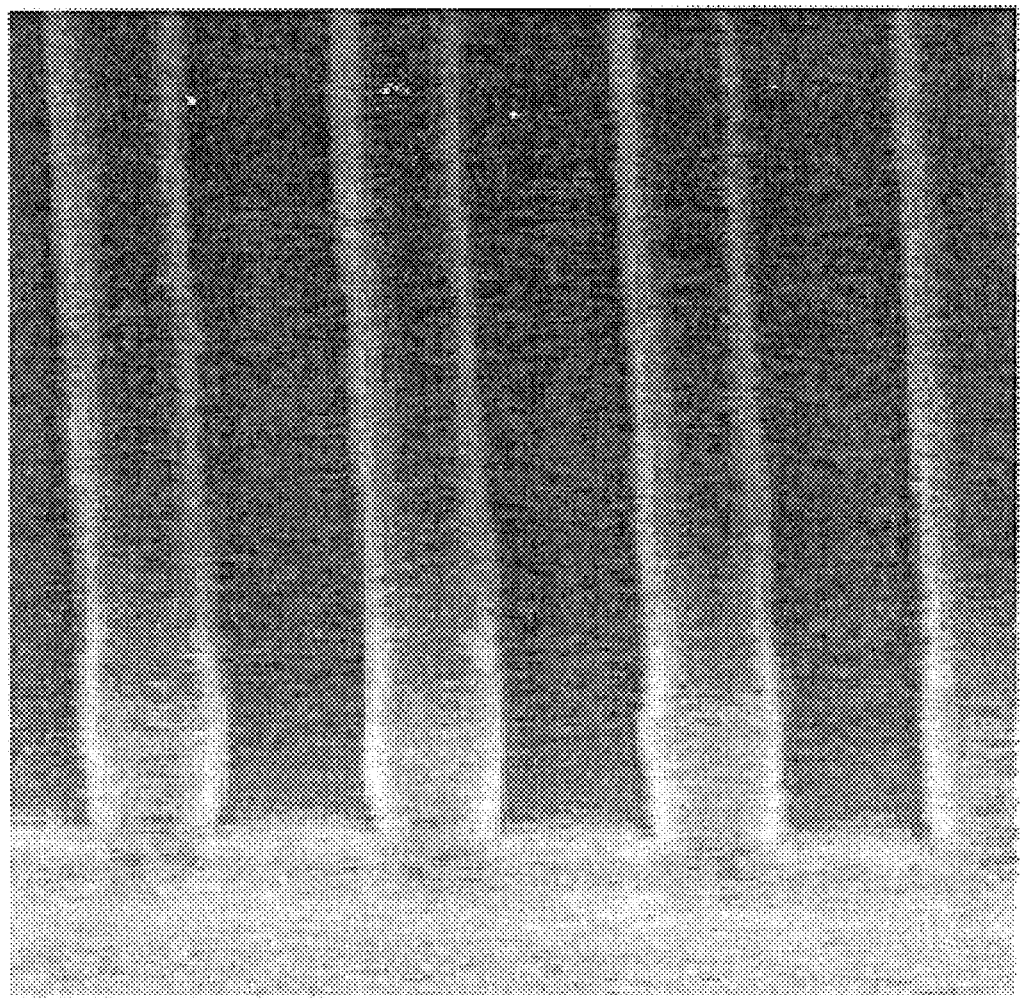

The procedure of Example 9 was repeated but using the polymer of Example 5, instead of the polymer of Example 3, to obtain the pattern of 0.20 μm L/S (see FIG. 3).

EXAMPLE 12

Figure 4:
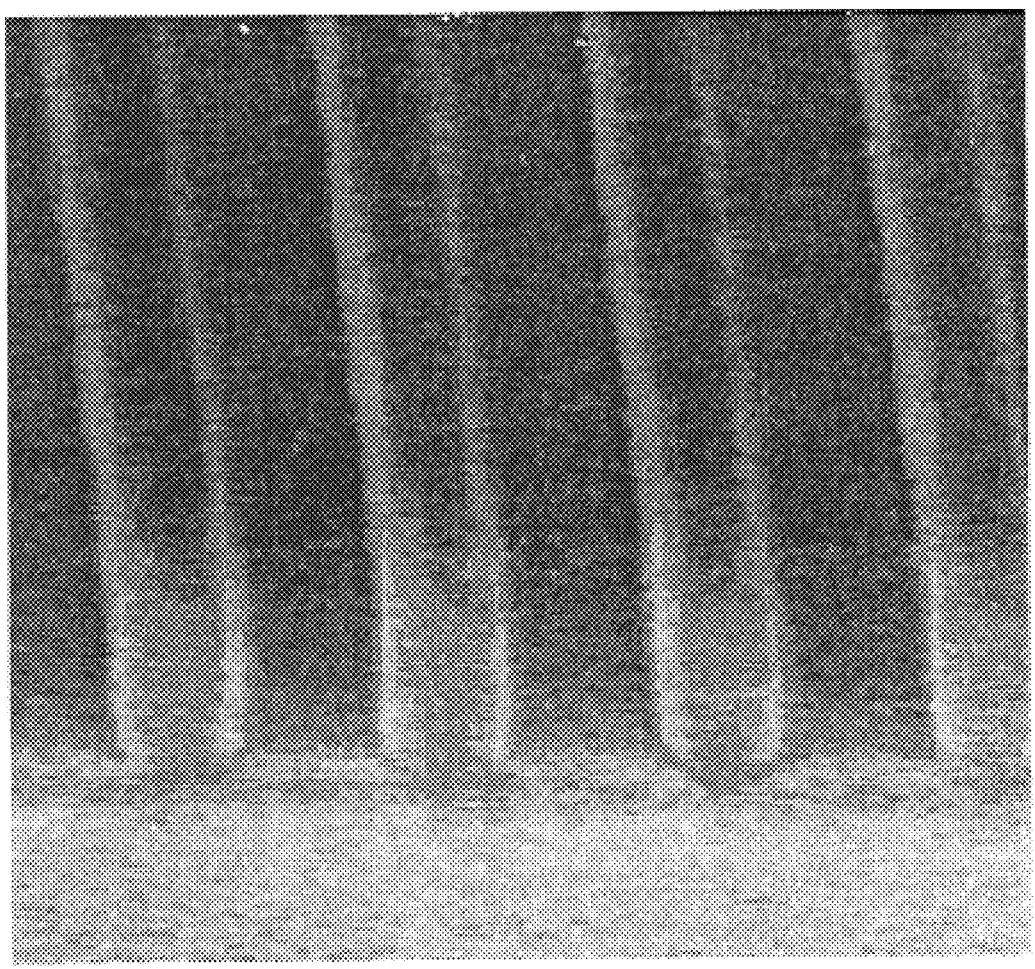

The procedure of Example 9 was repeated but using the polymer of Example 6, instead of the polymer of Example 3, to obtain the pattern of 0.20 μm L/S (see FIG. 4).

EXAMPLE 13

Figure 5:
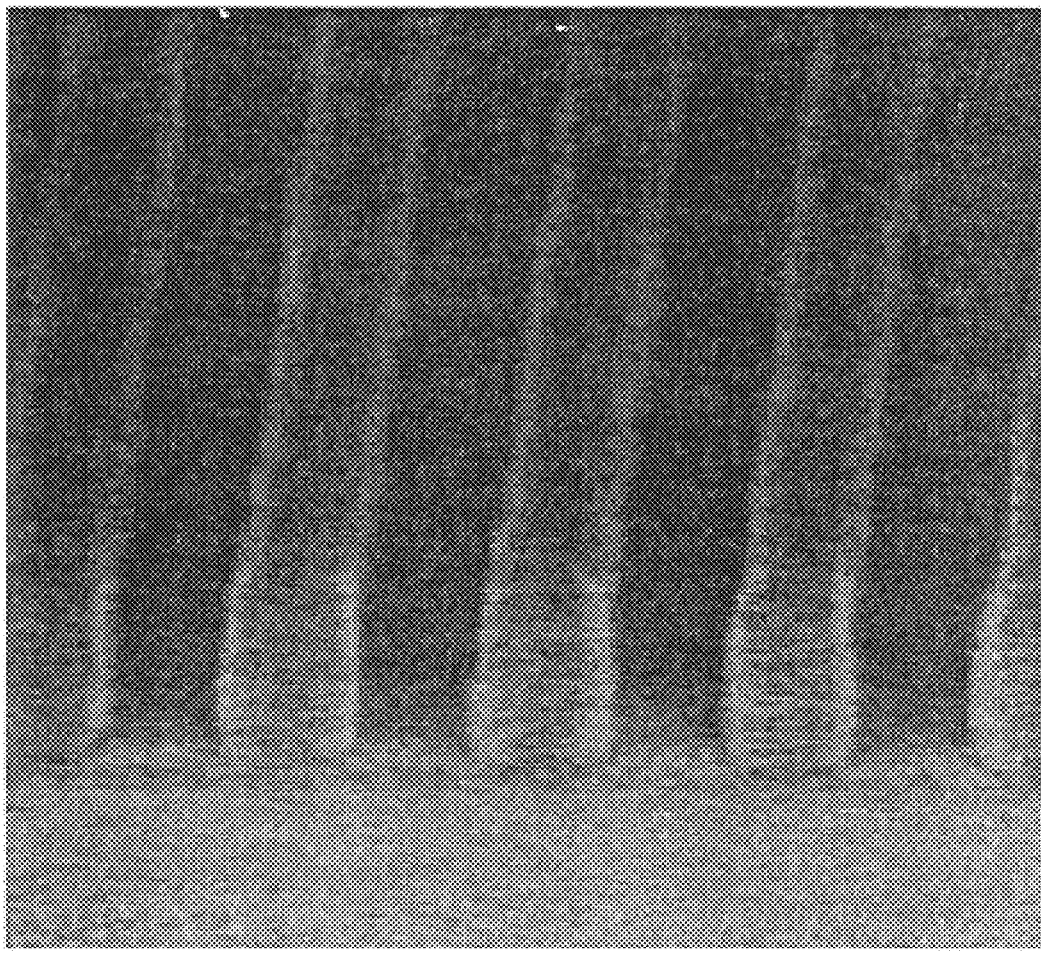

The procedure of Example 9 was repeated but using the polymer of Example 7, instead of the polymer of Example 3, to obtain the pattern of 0.20 μm L/S (see FIG. 5).

EXAMPLE 14

Figure 6:
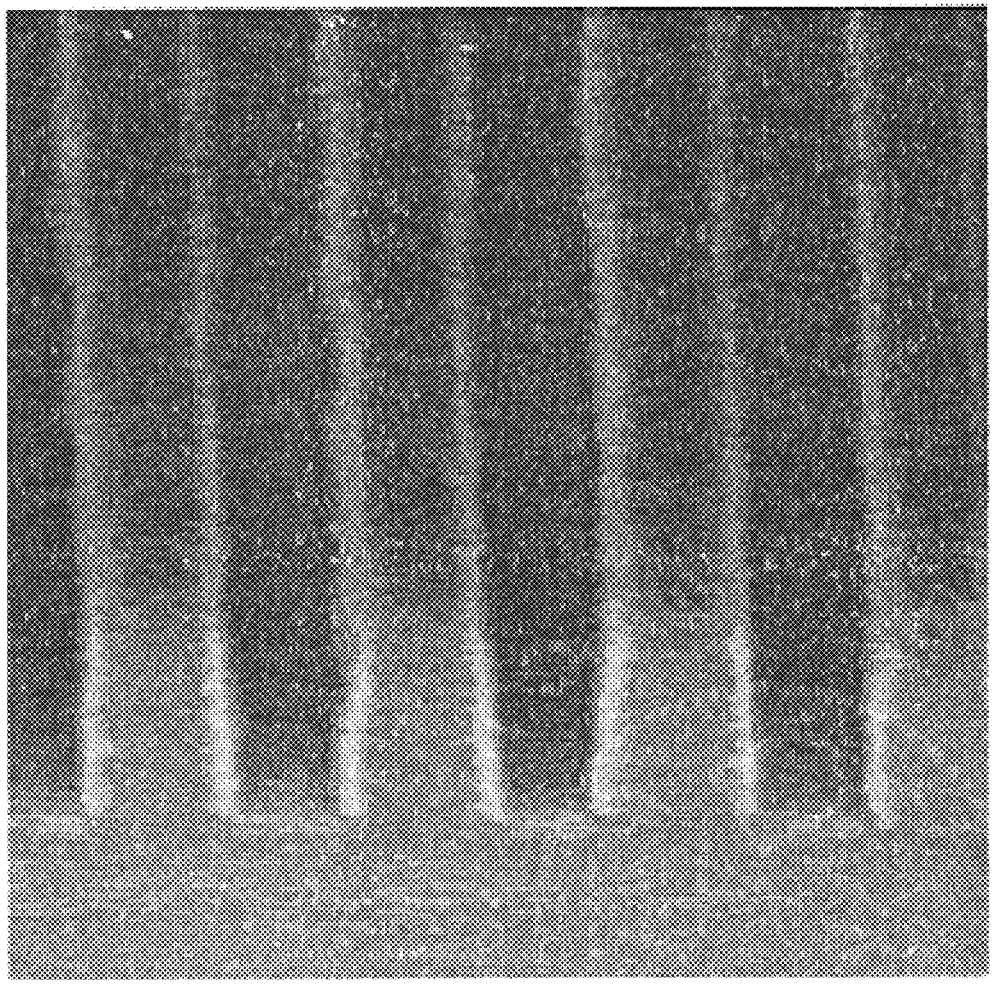

The procedure of Example 9 was repeated but using the polymer of Example 8, instead of the polymer of Example 3, to obtain the pattern of 0.20 μm L/S (see FIG. 6).

As described above, the photoresist polymer of the disclosure has excellent transparency and etching resistance in the deep ultraviolet region because its main chains have the alicyclic structure. In addition, the photoresist polymer comprises amide groups, and thus has improved PED stability.

What is claimed:

1. A photoresist monomer of following Formula 1:

Formula 1

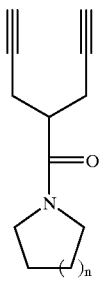

wherein, n is an integer from 0 to 5.

2. The photoresist monomer according to claim 1, which is one of piperidinyl dipropargyl acetamide and pyrrolidinyl dipropargyl acetamide.

3. A photoresist polymer comprising dipropargyl acetamide of following Formula 1 as a first monomer:

Formula 1

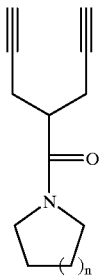

wherein, n is an integer from 0 to 5.

4. The photoresist polymer according to claim 3, further comprising at least one monomer selected from the group consisting of dipropargyl acetic acid ester derivative of following Formula 2 and dipropargyl carbinol of following Formula 3:

Formula 2

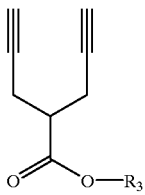

wherein, $R_3$ is H or an acid labile protecting group,

Formula 3

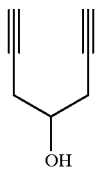

Formula 3

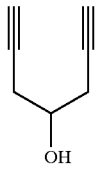

5. The photoresist polymer according to claim 4, wherein the acid labile protecting group is selected from the group consisting of tert-butyl, tetrahydropyran-2-yl, 2-methyl tetrahydropyran-2-yl, tetrahydrofuran-2-yl, 2-methyl tetrahydrofuran-2-yl, 1-methoxypropyl, 1-methoxy-1-methylethyl, 1-ethoxypropyl, 1-ethoxy-1-methylethyl, 1-methoxyethyl, 1-ethoxyethyl, tert-butoxyethyl, 1-isobutoxyethyl, tert-butoxycarbonyl and 2-acetylmenth-1-yl.

6. The photoresist polymer according to claim 3, which is selected from the group consisting of:

poly(tert-butyl dipropargyl acetate/dipropargyl carbinol/piperidinyl dipropargyl acetamide);

poly(ethoxyethyl dipropargyl acetate/dipropargyl carbinol/piperidinyl dipropargyl acetamide);

poly(ethoxypropyl dipropargyl acetate/dipropargyl carbinol/piperidinyl dipropargyl acetamide);

poly(tert-butyl dipropargyl acetate/dipropargyl carbinol/pyrrolidinyl dipropargyl acetamide);

poly(ethoxyethyl dipropargyl acetate/dipropargyl carbinol/pyrrolidinyl dipropargyl acetamide); and poly(ethoxypropyl dipropargyl acetate/dipropargyl carbinol/pyrrolidinyl dipropargyl acetamide).

7. A process for preparing the photoresist polymer of claim 3 comprising the step of polymerizing a photoresist monomer of following Formula 1 at the presence of a metathesis catalyst:

Formula 1

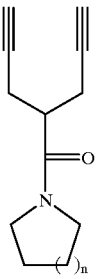

wherein, n is an integer from 0 to 5.

8. The process according to claim 7, wherein the polymerizing step further comprises the step of adding at least one monomer selected from the group consisting of dipropargyl acetic acid ester derivative of following Formula 2 and dipropargyl carbinol of following Formula 3:

Formula 2

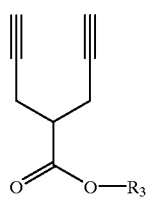

wherein, R₃ is H or an acid labile protecting group,

Formula 3

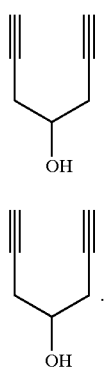

Formula 3

9. The process according to claim 7, wherein the metathesis catalyst further comprises a cocatalyst.

10. The process according to claim 9, wherein each of the metathesis catalyst and the cocatalyst is independently a transition metal-halide or an organometallic compound.

11. The process according to claim 10, wherein the catalyst is selected from the group consisting of $MoCl_5$, $WCl_6$, $Mo(OEt)_5$ and $PdCl_2$, and the cocatalyst is selected from the group consisting of $(n\text{-}BU)_4Sn$ and $EtAlCl_2$.

12. The process according to claim 7, wherein the polymerization is performed in a solvent selected from the group consisting of chlorobenzene, 1,4-dioxane, dimethylformamide, cyclohexane, tetrachloromethane, tetrahydrofuran and mixture thereof.

13. The process according to claim 9, wherein each of the metathesis catalyst and the cocatalyst is a form of solution whose solvent is selected from the group consisting of hexane, tetrahydrofuran, cyclohexane and mixture thereof.

14. A photoresist composition comprising the photoresist polymer of claim 3, an organic solvent and a photoacid generator.

15. The photoresist composition according to claim 14, wherein said photoacid generator is one or more compounds selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate, dibutylnaphthylsulfonium triflate and mixture thereof.

16. The photoresist composition according to claim 14, wherein an amount of photoacid generator ranges from about 0.01 to about 10% by weight of the photoresist polymer.

17. The photoresist composition according to claim 14, wherein the organic solvent is selected from the group consisting of propylene glycol methyl ether acetate, propylene glycol methyl ether, ethyl lactate, methyl 3-methoxypropionate, ethyl 3-ethoxypropionate, cyclohexanone and mixture thereof.

18. The photoresist composition according to claim 14, wherein an amount of solvent ranges from about 100% to about 1000% by weight of the photoresist polymer.

19. A process for forming a photoresist pattern comprising the steps of:
(a) coating the photoresist composition of claim 14 on substrate of semiconductor element to form a photoresist film;
(b) exposing said photoresist film to light using a light source; and
(c) developing said photoresist film.

20. The process according to claim 19, further comprising a baking step before and/or after step (b).

21. The process according to claim 20, wherein the baking step is performed at the temperature ranging from 70 to 200° C.

22. The process according to claim 19, wherein the light source is selected from the group consisting of VUV(157 nm), ArF(193 nm), KrF(248 nm), EUV(13 nm), E-beam, X-ray and ion beam.

23. The process according to claim 19, wherein the photoresist film is irradiated with light-exposure energy in the range from 1 mJ/cm² to 100 mJ/cm².

24. A semiconductor element manufactured by the process according to claim 19.

* * * * *

UNITED STATES PATENT AND TRADEMARK OFFICE
CERTIFICATE OF CORRECTION

PATENT NO.   : 6,607,868 B2                                              Page 1 of 1
DATED        : August 19, 2003
INVENTOR(S)  : Jae H. Choi It is certified that error appears in the above-identified patent and that said Letters Patent is hereby corrected as shown below:

<u>Column 10,</u>
Lines 10-15, delete second drawing.

<u>Column 11,</u>
Lines 20-25, delete second drawing.

Signed and Sealed this

Second Day of March, 2004

JON W. DUDAS
*Acting Director of the United States Patent and Trademark Office*